US007017580B2

(12) United States Patent
Prescott et al.

(10) Patent No.: US 7,017,580 B2
(45) Date of Patent: Mar. 28, 2006

(54) PUNCTUM PLUG SYSTEM INCLUDING A PUNCTUM PLUG AND PASSIVE INSERTION TOOL THEREFOR

(75) Inventors: Anthony D. Prescott, Arlington, TN (US); Richard W. Mendius, Collierville, TN (US)

(73) Assignee: Clarity Corporation, Memphis, TN (US)

( * ) Notice: Subject to any disclaimer, the term of this patent is extended or adjusted under 35 U.S.C. 154(b) by 120 days.

(21) Appl. No.: 10/443,298

(22) Filed: May 22, 2003

(65) Prior Publication Data

US 2004/0231679 A1    Nov. 25, 2004

(51) Int. Cl.
*A61F 13/00* (2006.01)

(52) U.S. Cl. .................. 128/846; 128/887; 604/8; 604/9

(58) Field of Classification Search ................. 128/846, 128/887, 888, 898; 606/107, 207, 210; 604/4, 604/8, 294

See application file for complete search history.

(56) References Cited

U.S. PATENT DOCUMENTS

| 3,949,750 A | 4/1976 | Freeman ..................... 128/260 |
| 4,056,496 A | 11/1977 | Mancini et al. ........ 260/29.6 TA |
| 4,461,295 A | 7/1984 | Herrick ..................... 128/303.1 |
| 4,660,546 A | 4/1987 | Herrick et al. .............. 128/1 R |
| D295,445 S * | 4/1988 | Freeman ..................... D24/23 |
| 4,886,488 A | 12/1989 | White ............................ 604/9 |
| 4,915,684 A * | 4/1990 | MacKeen et al. ............... 604/8 |
| 4,959,048 A * | 9/1990 | Seder et al. ..................... 604/9 |
| 5,049,142 A | 9/1991 | Herrick et al. .............. 604/294 |
| 5,053,030 A | 10/1991 | Herrick et al. ........... 604/890.1 |
| 5,163,959 A | 11/1992 | Herrick ......................... 623/11 |
| 5,171,270 A | 12/1992 | Herrick ......................... 623/11 |
| 5,224,938 A | 7/1993 | Fenton, Jr. ................... 604/247 |
| 5,283,063 A | 2/1994 | Freeman ..................... 424/427 |
| 5,334,137 A | 8/1994 | Freeman ......................... 604/8 |
| 5,417,651 A | 5/1995 | Guena et al. ..................... 604/8 |
| 5,423,777 A | 6/1995 | Tajiri et al. .................. 604/294 |
| 5,522,837 A | 6/1996 | Latina ......................... 606/201 |
| 5,626,559 A | 5/1997 | Solomon ........................ 604/9 |
| 5,723,005 A | 3/1998 | Herrick ......................... 623/4 |
| 5,741,292 A | 4/1998 | Mendius ..................... 606/191 |

(Continued)

FOREIGN PATENT DOCUMENTS

GB    2 069 339    8/1981

(Continued)

OTHER PUBLICATIONS

Brochure: "Ready-Set" Punctum Plugs, designed by J.A. Bernard, MD, FCI Ophthalmic, 2003, on www.fci-ophthalmic.com/ready-set_punctum_plugs.htm.

(Continued)

*Primary Examiner*—Michael A. Brown
(74) *Attorney, Agent, or Firm*—Gordon & Jacobson, P.C.

(57) ABSTRACT

A punctum plug system includes a punctum plug and an insertion tool therefor. In various embodiments of the invention, the plug includes an axial bore shaped in accord with a stepped cylinder, a cylinder having a tapered end, or a combination thereof. In each embodiment, a relatively proximal portion of the tip of the insertion tool extends within a relatively larger diameter proximal portion of the plug bore but does not frictionally engage such portion, and a relatively distal portion of the insertion tool tip frictionally engages the distal portion of the plug bore. The frictional engagement between the tool tip and the plug is preferably optimized such that once the plug is inserted into a punctum for which the plug is appropriately sized, the insertion tool may be removed simply by withdrawal of the tool, without wiggling the tool or stabilizing the plug with a second instrument.

24 Claims, 9 Drawing Sheets

U.S. PATENT DOCUMENTS

| | | | | |
|---|---|---|---|---|
| 5,766,243 | A | 6/1998 | Christensen et al. | 623/4 |
| 5,830,171 | A | 11/1998 | Wallace | 604/8 |
| 6,016,806 | A * | 1/2000 | Webb | 128/846 |
| 6,041,785 | A * | 3/2000 | Webb | 128/887 |
| 6,234,175 | B1 | 5/2001 | Zhou et al. | 128/887 |
| 6,271,281 | B1 | 8/2001 | Liao et al. | 523/106 |
| 6,344,047 | B1 | 2/2002 | Price et al. | 606/191 |

FOREIGN PATENT DOCUMENTS

| | | |
|---|---|---|
| GB | 2 160 778 A | 1/1986 |

OTHER PUBLICATIONS

Brochure: Ready-Set Punctum Plugs Silicone, For Punctual Occlusion in Keratitis Sicca, designed by J.A. Bernard, MD, Ophthalmic FCI.

Product Information: Introducing the Odyssey Shuttle System™ (OSS), Oddysey Medical, Inc., 2000.

Product Information: Herrick Lacrimal Plugs®, Lacrimedics, on www. Lacrimedics.com/html/hplug1.html.

Product Insert: EagleVision EaglePlugs and Tapered-Shaft Flow Controllers, 1998 EagleVision, Inc., 1995.

Product Guide: "Punctum Plugs with a Slant!", FCI Ophthalmics "Ready-Set" Punctum Plugs, down loaded at www.revoptom.com/PS/FCIOphth.htm.

"Clinicians Report Favorable Results with Theromosensititve Punctum Plug" by Suzanne Bryla, Primary Care Optometry News, May 1, 2003.

* cited by examiner

PUNCTUM PLUG SYSTEM INCLUDING A PUNCTUM PLUG AND PASSIVE INSERTION TOOL THEREFOR

BACKGROUND OF THE INVENTION

1. Field of the Invention

This invention relates broadly to prostheses and devices for use therewith. This invention particularly relates to ophthalmologic prostheses, and more particularly to medical canalicular inserts such as punctum plugs, and inserters therefor.

2. State of the Art

The surface of the eye and the inner surface of the eyelid are moisturized by tears constantly produced by glands around the eye. A tiny hole, known as the lacrimal punctum, located at the medial margin of each upper and lower lid margin drains the tears away through ducts for proper circulation.

A variety of eye problems are related to an insufficient volume of tears on the surface of the eyes. The most common is keratoconjunctivitis sicca, also known as dry eye syndrome. A common cause for the insufficient tear volume is the drainage of tear fluid through the punctal opening, the lacrimal duct, and into the nasal passage, thereby removing the fluid from where it is needed at the eye surface. Contact lens wearer particularly suffer when there is a lack of tear volume. In addition, dry eye is a component of various ocular surface diseases such as corneal ulcers, conjunctivitis, pterygium, blepharitis, keratitis, red lid margins, recurrent corneal erosion, filamentary keratitis and other external eye diseases.

A number of methods for closing the punctal opening have been used to prevent dry eye, including suturing, laser sealing, and plugging. Plugging with a punctum plug is the least severe solution, is relatively inexpensive, and is being performed with increasing frequency.

In addition, punctum plugs may be useful in decreasing contact lens intolerance, for increasing retention/enhancement of ocular medications on the eye, for maintenance of ocular flora, for punctal stenosis, and to enhance healing and comfort after surgery.

A punctum plug typically includes an elongate shaft having a proximal end and a distal end, a head at the proximal end of the shaft, and a relatively larger body at the distal end of the shaft for occluding a lacrimal punctum. The plug is usually provided with a proximal axial bore for receiving an insertion tool. In the current punctum plug insertion procedure, the sphincter muscle about the punctal opening is dilated with a dilator and an insertion tool, on which the plug is mounted, is used to maneuver the plug towards the dilated punctum. Force is then applied to the insertion tool to move the body of the plug through the punctal opening, the muscles of the punctal ring, and into the vertical punctum of the lacrimal canaliculus until the plug is fully inserted. The plug is fully inserted when the head seats against the tissue at the punctal opening and the body seats within the lacrimal punctum and vertical canaliculus so as to block the passage of tear fluid into the punctum and thereby retain tear fluid at the surface of the eye.

Once the plug is fully inserted in the punctum, the insertion tool is decoupled from the plug and withdrawn. The insertion tools can be categorized as passive or active. Passive tools have no moving parts, while active tools are actuated to move a plug mount portion of the tool relative to the plug in order to disengage the plug mount from the plug.

Prior art passive tools generally comprise a cylindrical wire element coupled to a relatively larger handle element. The insertion tool is removed from the plug by wiggling the inserter relative to the plug or while stabilizing the plug with forceps and applying a withdrawal force to the tool until the plug and tool are decoupled. Such insertion tools are disclosed in U.S. Pat. Nos. D295,445, 3,949,750, and 5,283,063, all to Freeman, U.S. Pat. No. 4,915,684 to MacKeen, U.S. Pat. No. 5,423,777 to Tajiri, and U.S. Pat. No. 5,723,005 to Herrick. While such tools are inexpensive to manufacture, they provide less than desirable control for release of the plug. In fact, the wiggling motion required to disengage the tool from the plug may inadvertently remove the plug from the punctum or relocate the plug to a less desirable portion of the punctal anatomy.

The more complex active insertion tools, when actuated, provide a single instrument which applies relative forces to the plug and the tool, e.g. by stabilizing the plug and withdrawing the inserter or by stabilizing the inserter and advancing the plug off the inserter. An exemplar active insertion tool is shown in U.S. Pat. No. 5,741,292 to Mendius. That tool includes a cylindrical body having an elongated button arranged longitudinally along the body. The button includes a slidable end and a fixed end positioned between the slidable end and a plug mounting end. The button has an outwardly bowing inner surface spaced from the body such that when the button is pressed toward the body, the slidable end slides away from the plug mounting end. A wire is fixedly attached to the slidable end of the button, and slidably extends within the body and protrudes out of the plug mounting end. A punctum plug is attached to the protruding end of the wire. When the button is depressed, the wire is retracted to release the plug.

Another active tool is provided by FCI Ophthalmics of Marshfield Hills, Mass. with its Ready-Set™ punctum plug system. The insertion tool is generally similar to the device described in U.S. Pat. No. 5,741,292, but includes a two-sided releasing mechanism with handles located on diametrically opposite sides of the body. When the handles are pressed toward each other, the plug mounting end of the tool moves relative to the wire and forces the plug off the wire, thereby dislodging the plug from the mount.

While the tools described in U.S. Pat. No. 5,741,292 and available from FCI Ophthalmics are effective for punctum plug insertion, such tools are significantly more expensive to manufacture than the passive tools. Moreover, as the active tools include moving parts, they can be more prone to malfunction than the passive tools.

Furthermore, in current plug implantation systems, it is not uncommon for plugs which are inappropriately sized for a particular punctum to be implanted. For example, punctal dilation tends to permit plugs that are too large for a particular punctum to be inserted therein. Then, once the punctal opening reassumes its natural size, the plug may cause irritation to the recipient. In addition, the stress of a plug too large for the particular punctum may undesirably permanently stretch the punctal anatomy. In addition, it is not uncommon for plugs which are too small to be inserted into a punctum and released from either an active insertion tool (by actuation) or a passive insertion tool (e.g., by stabilizing the plug head with a tool and wiggling the instrument away from the plug). If a plug is too small for the punctum into which it is implanted, it will likely be prematurely extruded, often within days of implantation. Thus, without specifically gauging the size of the punctum prior to insertion, none of the prior art systems provide a desirable way of releasing a plug which is appropriately sized for a given punctum.

SUMMARY OF THE INVENTION

It is therefore an object of the invention to provide a punctum plug system including an inexpensively manufactured insertion tool which is controllably released from a punctum plug mounted thereon.

It is another object of the invention to provide a punctum plug system wherein the insertion tool requires no user actuation to be released from a plug once the plug is inserted within the punctum.

It is another object of the invention to provide a punctum plug system which is self-gauging such that the plug is automatically released from an insertion tool when provided in a punctum of an appropriate size for the plug, but retained on the insertion tool if the punctum is too large.

It is a further object of the invention to provide a punctum plug system wherein the plug does not require dilation of the punctum opening prior to insertion.

It is an additional object of the invention to provide a punctum plug system wherein the plug is comfortable to a recipient patient.

In accord with these objects, which will be discussed in detail below, a punctum plug system is provided including a punctum plug and an insertion tool for inserting the plug into a punctum. The plug includes a head, a shaft, and a body, and an axial bore defined through the head and at least a portion of the shaft, and preferably also a portion of the body. In various embodiments of the invention, the shape of the bore is a stepped cylinder, a cylinder having a tapered end, or a combination thereof. Where the bore includes a single step, the tip of the insertion tool preferably includes a diameter corresponding to the smaller of the bore diameters. Where the bore is cylindrical and tapered, the tool tip is dimensioned to engage the bore preferably only at the tapered portion, and not at the cylindrical portion. Where the bore is tapered via multiple steps of decreasing diameters, the tip of the tool also includes multiple steps preferably corresponding in dimension to all but the largest step. Thus, in each embodiment, a relatively proximal portion of the tip of the tool (toward the head of the plug) extends within a relatively larger diameter cylindrical portion of the bore but does not frictionally engage such portion, and a relatively distal portion of the tip of the tool (toward the tip of the body of the plug) frictionally engages the plug. While the length of engagement between the tool tip and the bore of the plug is relatively shorter than prior art plugs in which the tool tip engages the entire length of the bore, the engagement is relatively deep within the plug, thereby limiting lateral movement of the plug on the tool tip and providing a stable mount for the plug. Moreover, the length of frictional engagement between the tip and the plug is preferably optimized such that once the plug is inserted into a punctum for which the plug is appropriately sized, the insertion tool may be removed simply by withdrawal of the tool, without wiggling the tool or stabilizing the plug with a second instrument, such as a forceps.

In addition, the outer surface of the body preferably includes a narrow taper to facilitate insertion, potentially without requiring prior dilation.

Furthermore, in a preferred embodiment, the shaft is preferably cylindrical, so that the punctal sphincter muscle will have limited contact with the shaft and thus the muscle will not be under constant tension. This configuration between the plug and the anatomy facilitates comfort to certain patients with respect to the implanted plug. The plug is retained within the punctum with a relatively large shelf at the interface between shaft and the body.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
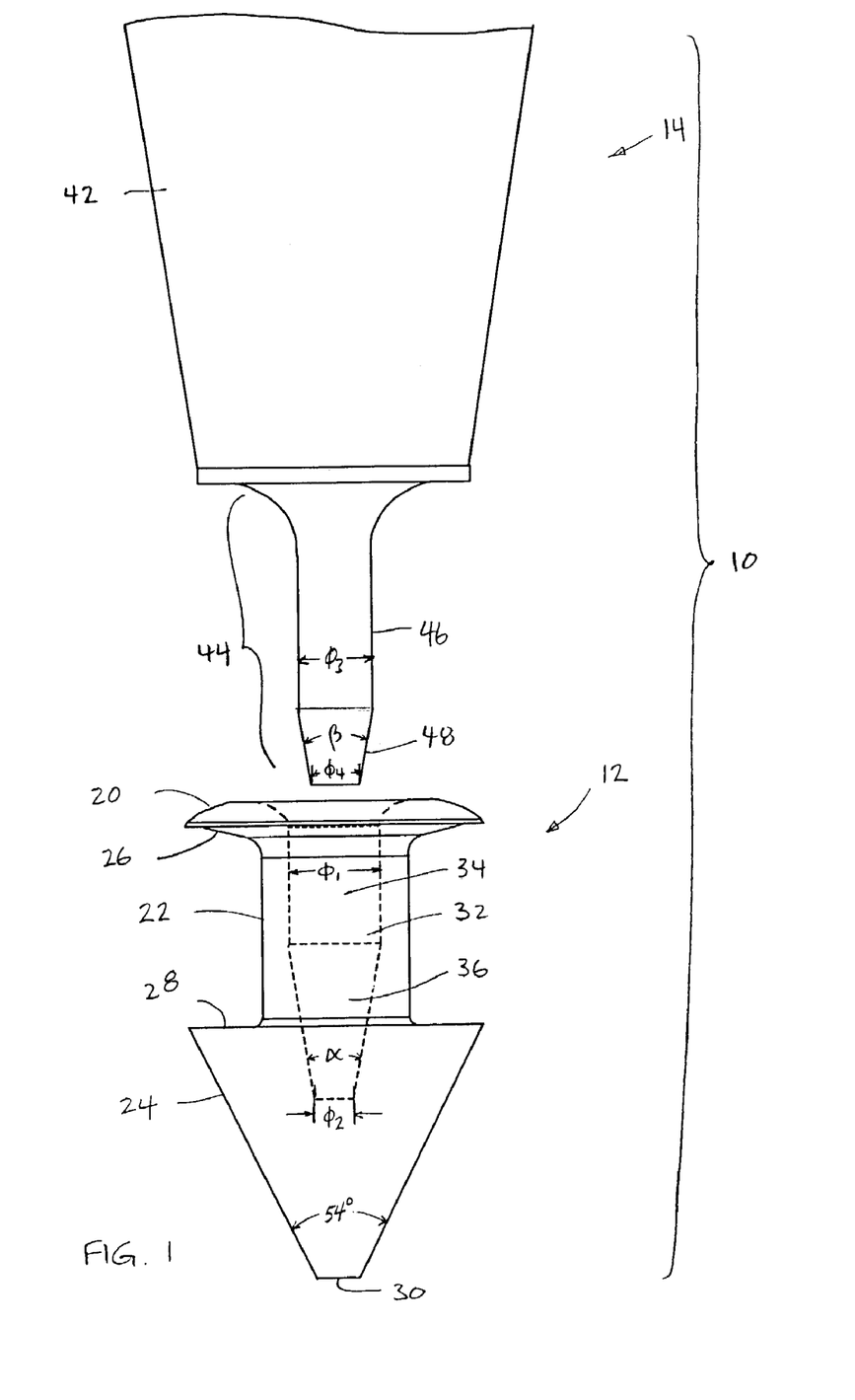
FIG. 1 is an exploded side elevation view of a first embodiment of a punctum plug system showing a punctum plug, having an axial bore shown in broken lines, and a distal end of an insertion tool according to the invention.

Turning now to FIG. 1, a first embodiment of a punctum plug system 10 according to the invention is shown. The system 10 includes a punctum plug 12 and an insertion tool 14 particularly adapted for use with the plug, as described in detail below.

The punctum plug 12 includes a head 20, a shaft 22, and a substantially solid body 24. The head 20 is an annular lip substantially wider than the shaft 22 and has sufficient structural stiffness to function as a stop to prevent movement of head 20 through the punctum when the plug 12 is subject to appropriate insertion forces. In a preferred embodiment, the head 20 has a frustoconical lower surface 26 that is preferably designed to have a low profile within the punctum to minimize any potential irritation of the eye, as described in U.S. Pat. No. 6,027,470 which is incorporated by reference herein in its entirety. According to a preferred aspect of the plug 12, the shaft 22 is substantially cylindrical. The transition from the shaft 22 to the body 24 defines a relatively large shelf 28 at the proximal surface of the body 24. The body 24 includes a tip 30 and from the tip rearward the cone of the body defines a relatively narrow angle taper, for example, between 50° and 60°, and most preferably approximately 54°, so as to facilitate insertion of the plug into the punctal opening even without prior dilation of the punctal sphincter muscle.

An axial bore 32 is defined through the head 20, the shaft 22 and a portion of the body 24. According to the first embodiment of the invention, the bore 32, in a natural unstressed state, includes a proximal cylindrical portion 34 having a first diameter $\phi_1$ and a relatively distal frustoconical portion 36 which tapers to a smaller second diameter $\phi_2$. In one preferred, but exemplar embodiment, $\phi_1$=0.315 mm (0.0124 inch), $\phi_2$=0.127 mm (0.005 inch), the length of portion 36 is 0.0533 mm (0.021 inch), and the angle $\alpha$ of the taper relative to the vertical is preferably approximately 20°.

The plug is preferably made from medical grade silicone (Shore 50A), or some other soft, low Durometer biocompatible material such as polytetrafluoroethylene (PTFE), hydroxyethylmethacrylate (HEMA), or polymethyl-methacrylate (PMMA) by, for example, injection molding, cast molding, or transfer molding.

Figure 2:
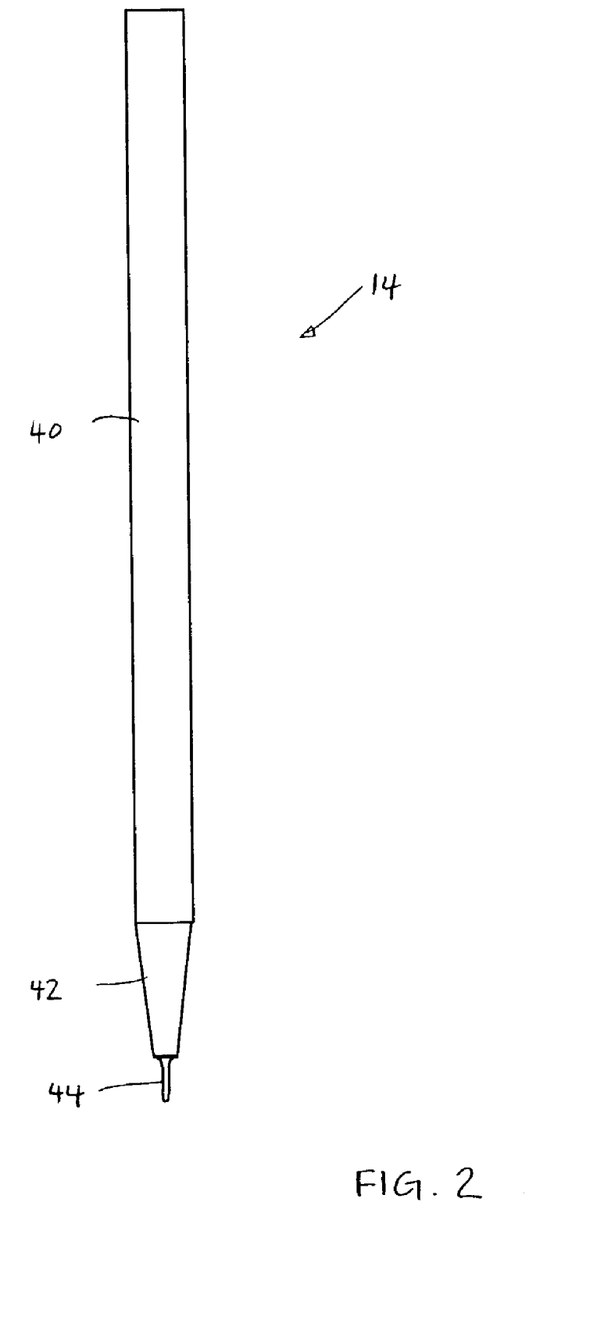
FIG. 2 is a side elevation of the first embodiment of the insertion tool.

Referring now to FIGS. 1 and 2, the insertion tool 14 of the system 10 includes a handle portion 40, a frustoconical transition portion 42, and a plug mount 44. The tool 14, including the plug mount 44, is preferably machined from polyvinyl-chloride. Alternatively, it could also be a combination of a plastic handle and a metal pin which defines the plug mount 44, or entirely from metal. The plug mount 44 includes a cylindrical portion 46 having a diameter $\phi_3$ smaller than diameter $\phi_1$ of the bore, and a tapered tip 48 which has a terminal diameter $\phi_4$ smaller than diameter $\phi_3$ but larger than diameter $\phi_2$. In a preferred exemplar embodiment, $\phi_3$=0.250 mm (0.00985 inch) and $\phi_4$=0.165 mm (0.007 inch), and the tapered tip is approximately 0.305 mm (0.012 inch) in length. The tip 48 is substantially frustoconical and defines a taper angle $\beta$ preferably smaller than angle $\alpha$, e.g. preferably approximately 10° to 17°. The relation of taper angles $\alpha$ and $\beta$, and the specific preferred materials (silicone for the plug and PVC for the plug mount) provide a desirable frictional engagement between the tip 48 and the plug 12, and thus the angles may be varied to alter the force required to disengage the tip 48 from the bore 32. In addition, the length of the tapered tip 48 is preferably shorter than the length of the tapered portion 36 of the bore 32 of the plug 12.

Figure 3:
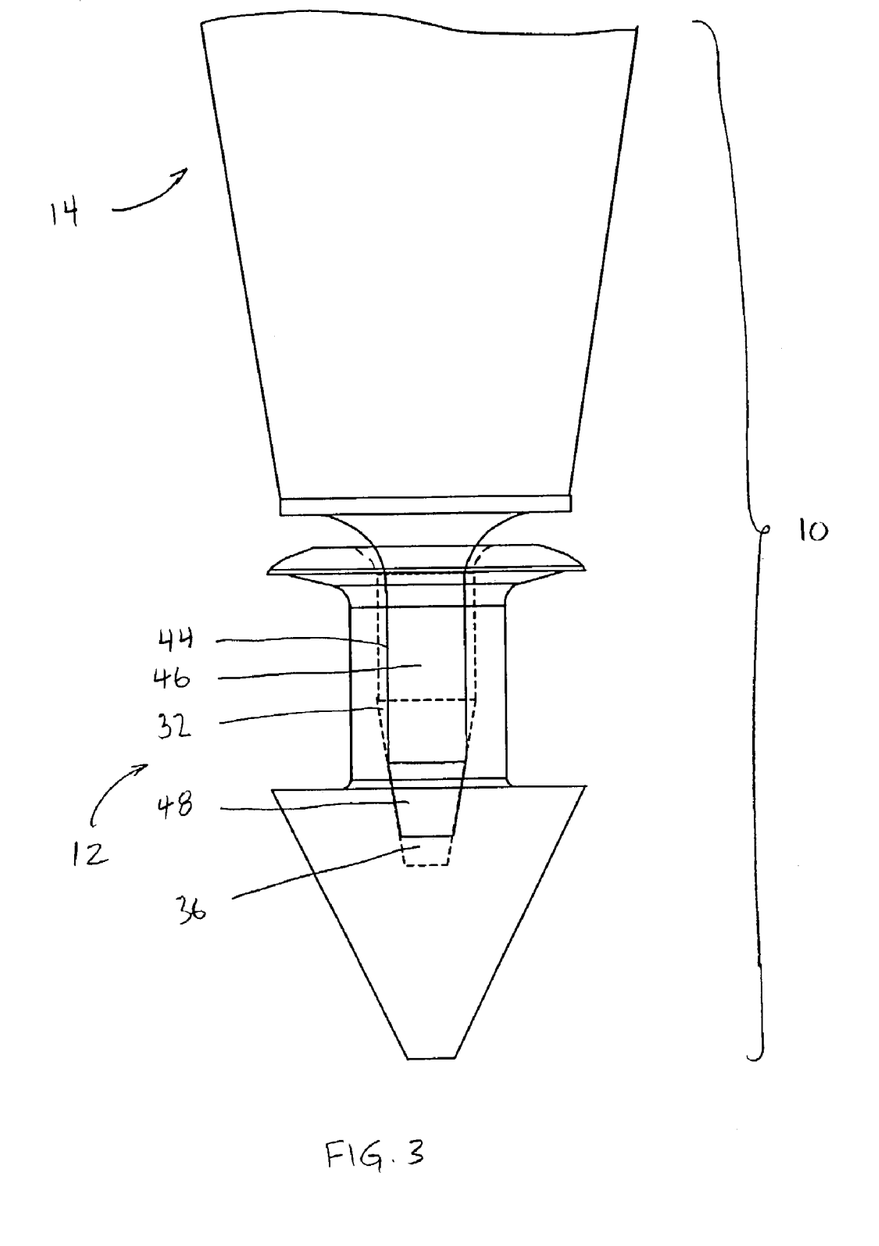
FIG. 3 is an assembled side elevation view of the first embodiment of the punctum plug system.

Referring now to FIG. 3, the plug 12 is shown mounted on the plug mount 44 of the insertion tool 14. It is seen that only the tip 48 of the plug mount 44 contacts the plug within the bore 32 and only at the tapered portion 36 of the bore. However, the contact between the tip 48 and the tapered portion 36 of the bore 32 provides effective frictional engagement to retain the plug 12 on the insertion tool 14 until the plug is inserted into the punctal opening. While the engagement between the tip and the bore is limited to a relatively shorter length of the tip (substantially shorter than prior art plug/insertion tool systems in which the tool tip engages the entire length of the bore), the engagement is relatively deep within the plug 12 and at or close to the center of mass of the plug. It is noted that the plug bore 32 extends distally of the location of contact by the plug mount 44, but that the relative dimensions of the bore 32 and mount 44 limit extension of the mount to the center of mass. Lateral movement of the plug 12 on the plug mount 44 is limited by contact of the side walls of the plug about the bore against the cylindrical portion 46 of the plug mount 44. As such, the plug 12 is stably mounted on the plug mount 44 until release is desired.

Figure 4:
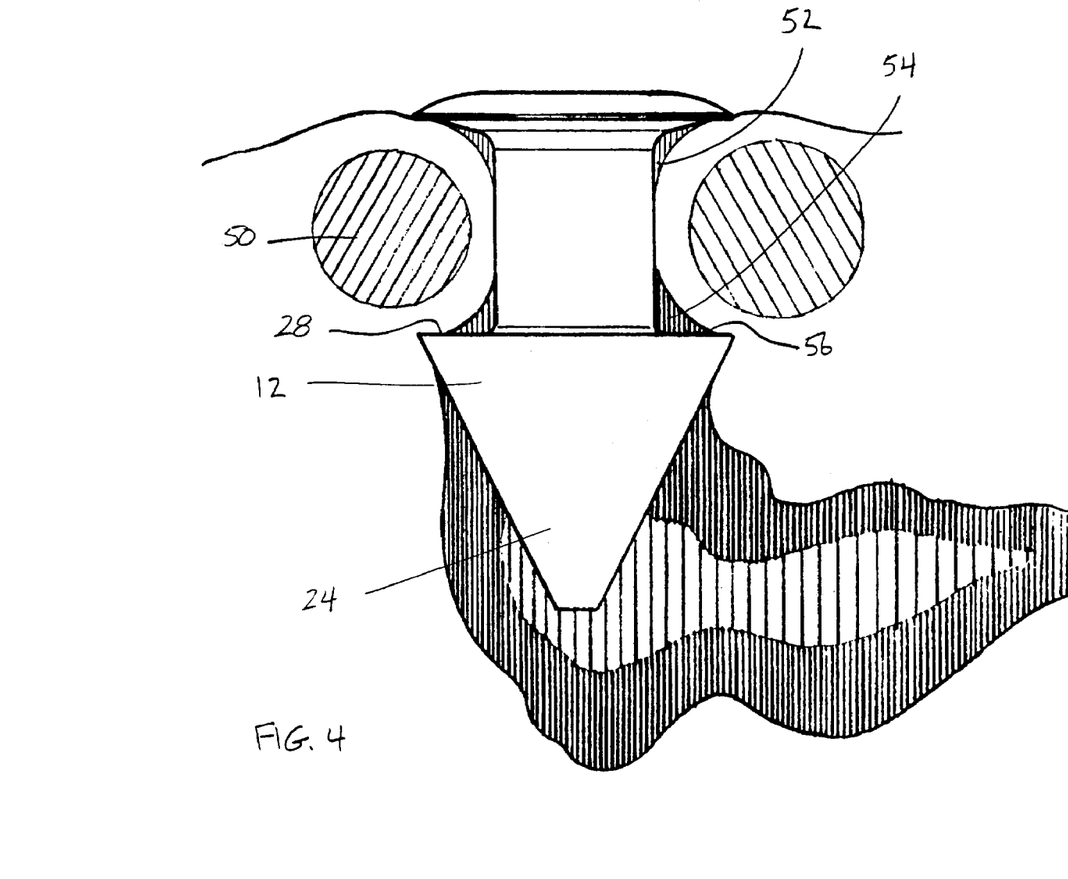
FIG. 4 is a schematic anatomical section view illustrating a plug according to the invention seated within a lacrimal punctum.

Referring to FIGS. 3 and 4, as mentioned above, the relatively narrow angle of the frustoconical body 24 of the plug 12 is designed for insertion without prior dilation of the punctal ring 50 (or punctal sphincter muscle). Moreover, the plug is preferably adapted in structure to be self-gauging or self-sizing. That is, the plug, without dilation and undue force, will not enter the opening 52 of a punctum 54 too small for the plug. Further, the plug 12 will enter a punctum too large for the plug, but the contact of the shelf 28 against the canalicular wall 56 just below the punctal ring 50 will fail to present a sufficient resistance against the frictional engagement between the above described plug mount 44 and the plug 12 when the insertion tool is moved in a direction away from the punctum (FIG. 3). Thus, the plug will be retained on the plug mount and be withdrawn from the punctum. If the plug is appropriately sized for the punctum, the canalicular wall 56 just below the punctal ring 50 will provide sufficient resistance to the shelf 28 of the plug 12 to overcome the frictional engagement between the plug mount and plug such that the insertion tool can be removed from the plug by simply withdrawing the tool in a direction away from the punctum, without wiggling the tool or stabilizing the plug with a second instrument, such as a forceps.

Once inserted, the punctal ring has limited stressful contact with the shaft and thus the punctal ring will not be under constant tension. This configuration between the plug and the anatomy facilitates comfort to certain patients with respect to the implanted plug.

Figure 5:
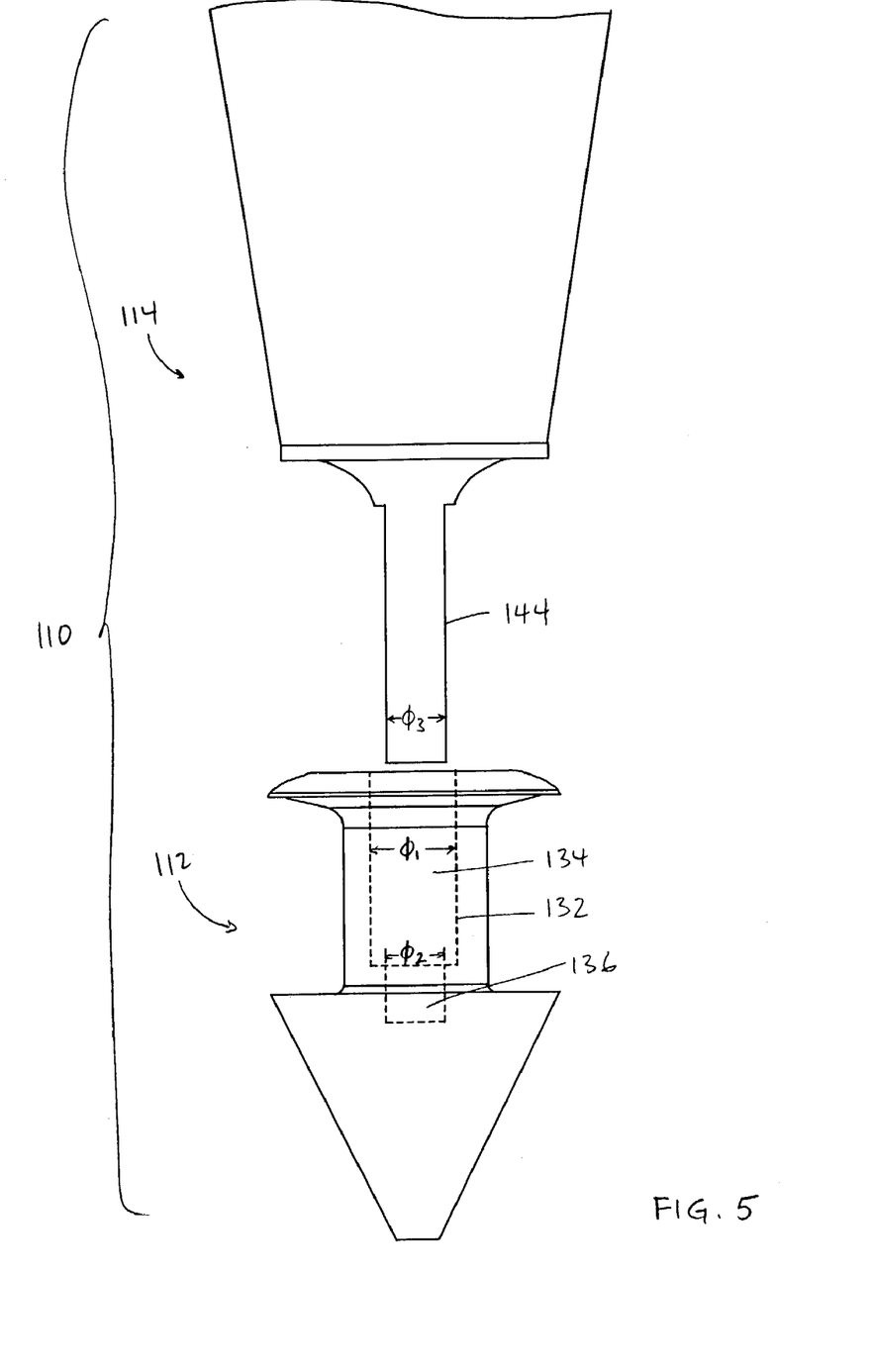
FIG. 5 is an exploded side elevation view of a second embodiment of a punctum plug system, showing a punctum plug, having an axial bore shown in broken lines, and a distal end of an insertion tool according to the invention.
Figure 6:
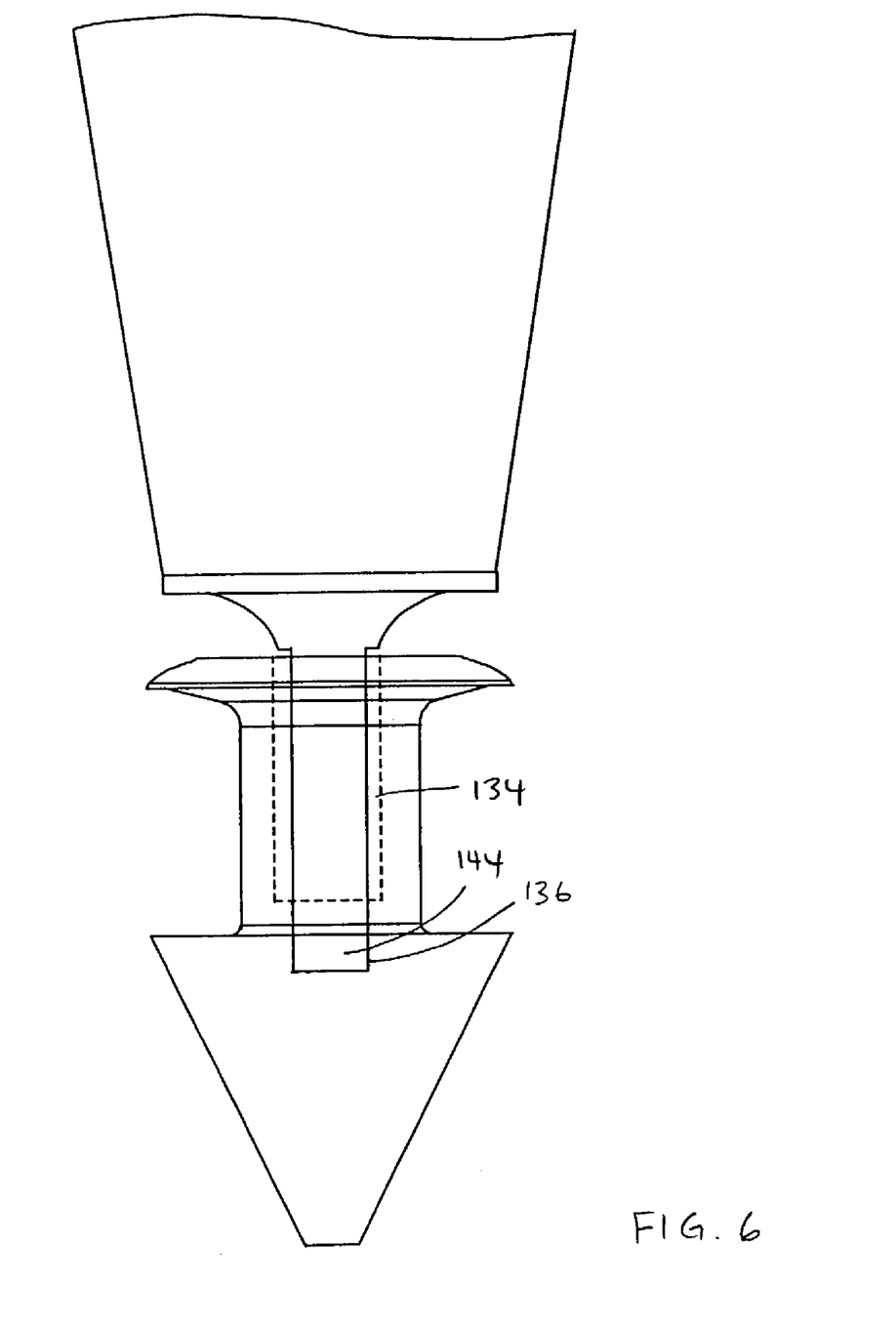
FIG. 6 is an assembled side elevation view of the second embodiment of the punctum plug system.

Turning now to FIGS. 5 and 6, a second embodiment of a plug system 110, substantially similar to the first embodiment (with like parts having reference numerals incremented by 100 relative thereto) is shown. The bore 132 of the plug 112 is stepped, defining a proximal cylindrical portion 134 of a first diameter $\phi_1$ and an adjacent relatively distal cylindrical portion 136 of a smaller second diameter $\phi_2$. The inserter 114 includes a cylindrical plug mount 144 preferably having a substantially constant diameter $\phi_3$. Diameter $\phi_3$ is set to provide frictional engagement of the plug mount 144 within the distal portion 136 of the bore (at diameter $\phi_2$), but is sufficiently smaller than diameter $\phi_1$ to prevent engagement with the proximal cylindrical portion 134 of the bore 132. In accord with one example, $\phi_1$=0.203 mm (0.008 inch), $\phi_2$32 0.178 mm (0.007 inch), and $\phi_3$=0.178 mm (0.007 inch). Further in accord with the example, the full length of bore 132 is 1.041 mm (0.041 inch), the length of portion 134 is 0.884 mm (0.0348 inch), the length of bore portion 136 is 0.157 mm (0.0062 inch), and the length of the plug mount 144 is 1.168 mm (0.046 inch). That is, for a desirable frictional engagement, the length of bore portion 136 is preferably approximately fifteen percent (15%) the total length of the bore 132, and $\phi_2$ and $\phi_3$ are preferably approximately the same.

Figure 7:
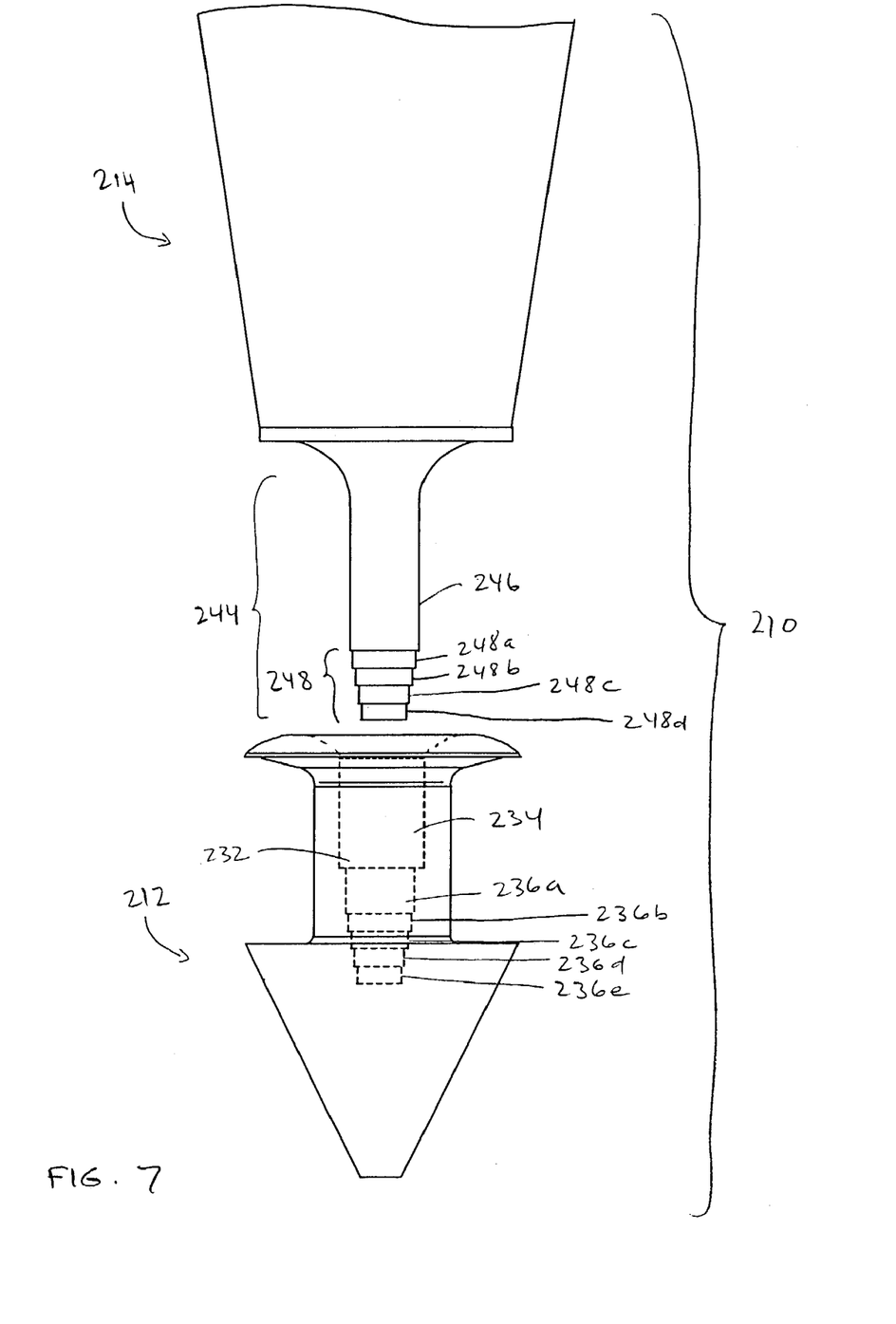
FIG. 7 is an exploded side elevation view of a third embodiment of a punctum plug system, showing a punctum plug, having an axial bore shown in broken lines, and a distal end of an insertion tool according to the invention.
Figure 8:
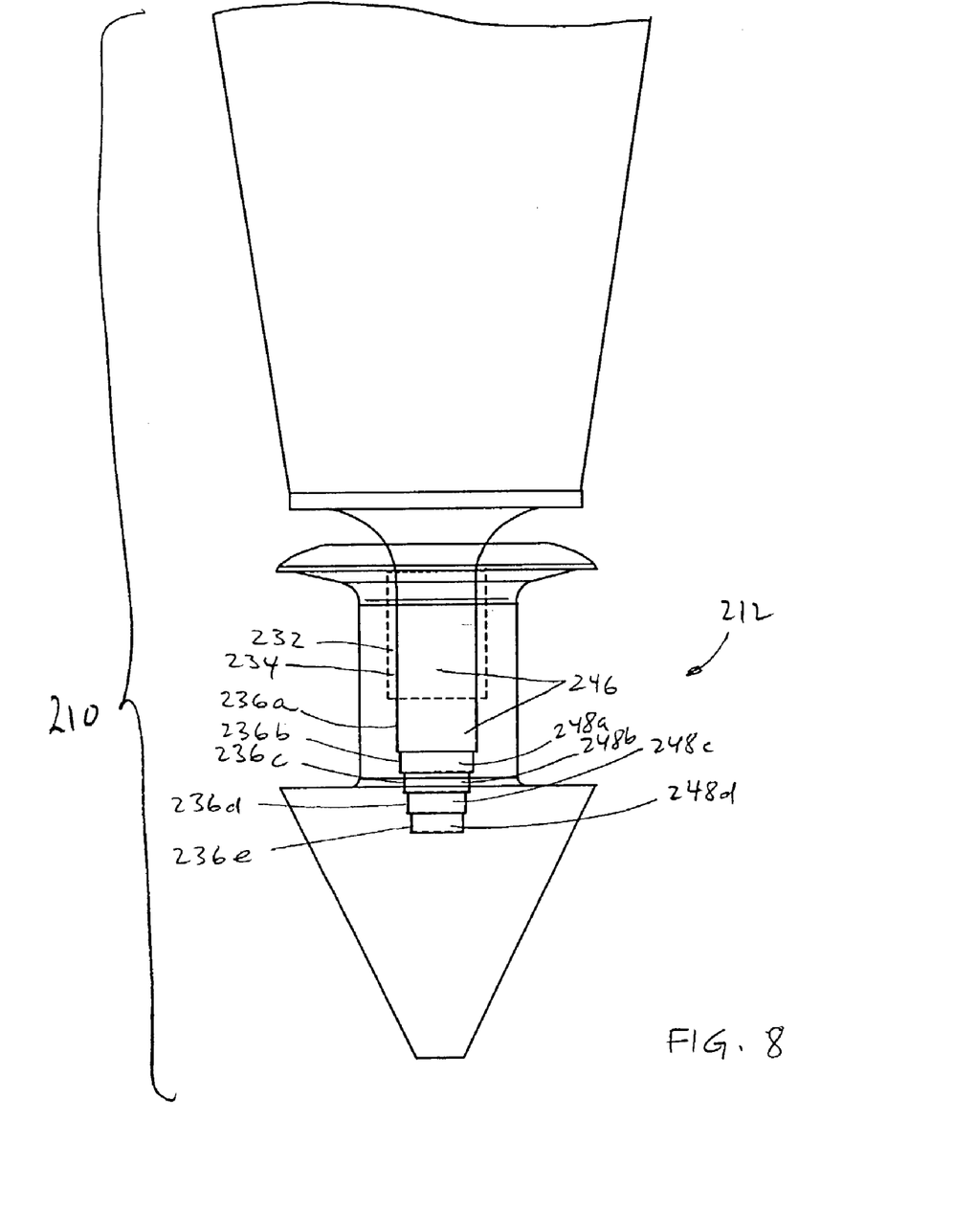
FIG. 8 is an assembled side elevation view of the third embodiment of the punctum plug system.

Referring now to FIGS. 7 and 8, a third embodiment of a plug system 210, substantially similar to the first embodiment (with like parts having reference numerals incremented by 200 relative thereto) is shown. The bore 232 of the plug 212 includes a plurality of stepped portions, such as a relatively large proximal portion 234 and five stepped portions 236a, 236b, 236c, 236d, 236e, each in successively decreasing diameter. The inserter 214 includes a cylindrical plug mount 244 having an elongate cylindrical portion 246 and a stepped tip 248 with portions 248a, 248b, 248c, 248d, each in successively decreasing diameter. The diameters of the portion 246 and stepped portions 248a, 248b, 248c, 248d are sized to provide a desirable frictional engagement of the plug mount 244 within portions 236a, 236b, 236c, 236d, 236e of the bore, while preventing frictional engagement between the plug mount 244 and the proximal portion 234 of the bore 232.

Figure 9:
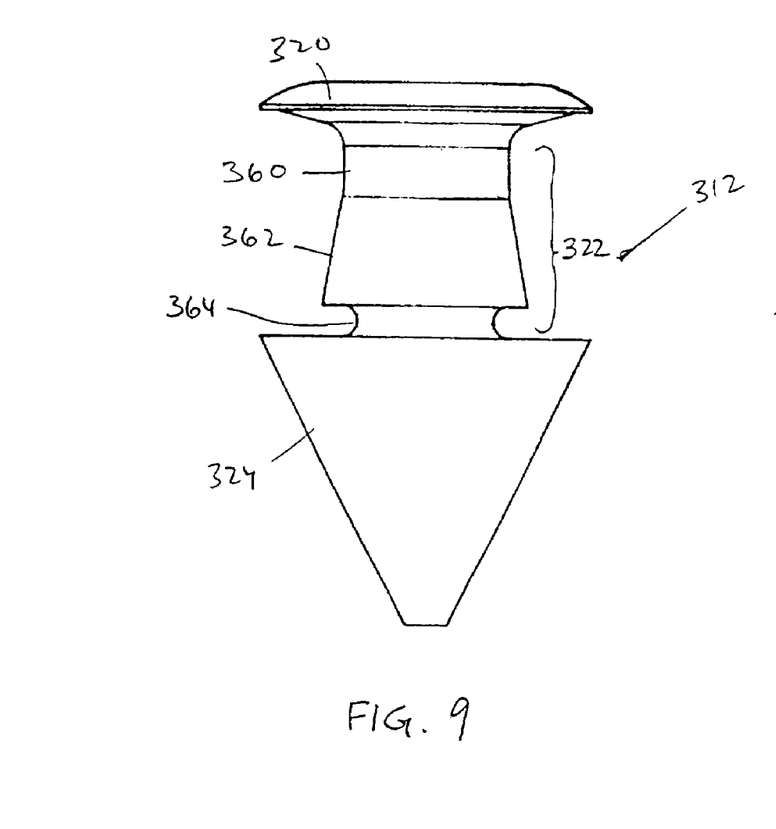
FIG. 9 is a side elevation view of a fourth embodiment of a punctum plug for use in a punctum plug system according to the invention.
Figure 10:
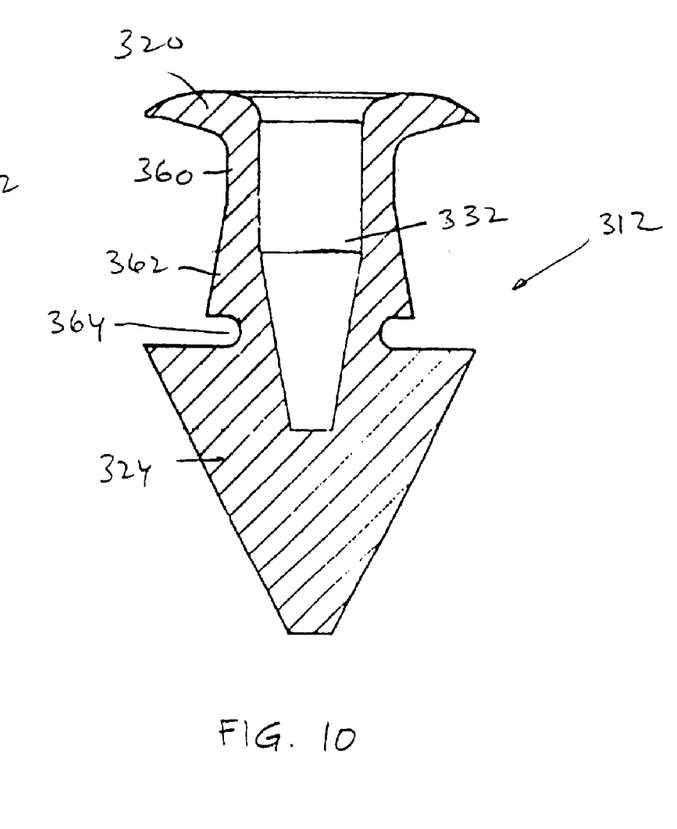
FIG. 10 is a longitudinal section view of the punctum plug of FIG. 9.

Turning now to FIGS. 9 and 10, another embodiment of the plug 312 is shown. The plug 312 has a bore 332 provided with any of the bore shapes described above, or variations thereof. In distinction from the above described plugs, the shaft 322 of the plug includes a cylindrical portion 360 and a portion 362 which tapers toward the head 320 of the plug. This shape increases contact of the shaft 322 against the punctal ring 50 (FIG. 4), and draws the plug down into the vertical punctum to facilitate retention. In addition, the shaft 322 is provided with a circumferential groove 364 at or directly adjacent the body 324. A groove 364 at this location effectively increases flexibility for proper anatomical fit. Either of these modifications may be provided to any of the previously described plugs or any other plugs which are within the scope of the invention.

Each embodiment of the system provides a desirable frictional engagement whereby, if the plug is appropriately sized for the punctum, the canalicular wall will provide sufficient resistance to the plug to overcome the frictional engagement between the plug mount and plug such that the insertion tool can be removed from the plug by simply withdrawing the tool in a direction away from the punctum, without wiggling the tool or stabilizing the plug with a second instrument. This is in contrast to prior art systems which generally require some physician-provided stabilization to the plug during tool removal or require excessive wiggling or other non-longitudinal movement of the tool relative to the plug to withdraw the plug from the tool without relocating or removing the plug.

There have been described and illustrated herein several embodiments of a punctum plug system, and plugs and insertion tools used within the system. While particular embodiments of the invention have been described, it is not intended that the invention be limited thereto, as it is intended that the invention be as broad in scope as the art will allow and that the specification be read likewise. Thus, while particular preferred dimensions and angles have been disclosed, it will be appreciated that other dimensions and angles to various components can be used as well. In addition, while the plug bores and plug mounts of the insertion tool have been shown to be circular in cross-section, it is appreciated that other sectional shapes can be used. For example, and not by way of limitation, the plug mount and bore may be radially non-uniform, such as hexagonal or elliptical in cross-sectional shape, or may be entirely asymmetrical, all while preferably still having a tapered tip and end portion. Also, while particular materials for forming the plug and tool are disclosed, it is recognized that other suitable materials may be used. In addition, while it is desirable to couple the insertion tool near the center of mass of the plug, it is not essential to the invention and the inserter may be mounted more proximally or distally in the plug. It will therefore be appreciated by those skilled in the art that yet other modifications could be made to the provided invention without deviating from its spirit and scope as claimed.

What is claimed is:

1. A punctum plug system for use in conjunction with a punctum of an eye, comprising:
    a) a punctum plug sized for occlusion of the punctum, said punctum plug including a head portion, a body portion, and a shaft portion therebetween, said punctum plug defining an axial bore; and
    b) an insertion tool for inserting said punctum plug into the punctum, said insertion tool including a plug mount having a length which extends within said axial bore of said plug, said plug mount having a non-uniform diameter over said length,
        said length of said plug mount includes a proximal portion having a first diameter and a distal portion having a second diameter smaller than said first diameter, and
        said bore has a proximal portion having a third diameter which is larger than said first diameter of said length of said plug mount, and a distal portion having a fourth diameter which is smaller than said second diameter of said length of said plug mount, said distal portion being frustoconical in shape.

2. A punctum plug system according to claim 1, wherein: said length of said plug mount includes a tapered distal portion.

3. A punctum plug system according to claim 1, wherein: said length of said plug mount includes a proximal cylindrical portion and a relatively distal frustoconical portion.

4. A punctum plug system according to claim 1, wherein: said plug mount is circular in cross-section along said length.

5. A punctum plug system according to claim 1, wherein: said shaft portion of said plug is cylindrical.

6. A punctum plug system according to claim 1, wherein: said head portion of said plug is of a structure which sufficiently resists said head from being forced through a punctal sphincter muscle.

7. A punctum plug system according to claim 1, wherein: said body portion of said plug defines a conical section with an angle of between 50° and 60°.

8. A punctum plug system according to claim 7, wherein: said body portion of said plug defines a conical section with an angle of approximately 54°.

9. A punctum plug system for use in conjunction with a punctum of an eye, comprising:
    a) a punctum plug sized for occlusion of the punctum, said punctum plug including a head portion, a body portion, and a shaft portion therebetween, said plug defining a stepped bore having a length, a proximal portion of a first diameter, and a distal portion of relatively smaller second diameter, wherein said distal portion has a length which is fifteen percent said length of said stepped bore; and
    b) an insertion tool for inserting said punctum plug into the punctum, said insertion tool having a plug mount portion which is coupled within said bore, said plug mount portion having said second diameter.

10. A punctum plug system according to claim 9, wherein: said second diameter is 0.178 mm.

11. A punctum plug system according to claim 9, wherein: said length of said stepped bore is 1.041 mm, and said length of said distal portion is 0.157 mm.

12. A punctum plug for insertion through a punctal opening at the eye, comprising:
    a) a shaft portion having first and second ends;
    b) a head portion coupled to said first end of said shaft portion; and
    c) a body portion coupled to said second end of said shaft portion,
        said plug defining a bore for receiving an insertion tool by which to insert said plug into the punctal opening, wherein, when said plug is in a non-stressed state, said bore has a proximal length with a substantially constant first diameter and an adjacent relatively distal length having a second smaller diameter and being tapered relative to said first diameter, and wherein said body is solid radially outward from said bore.

13. A punctum plug according to claim 12, wherein:
said proximal and distal lengths are each cylindrical in cross-section.

14. A punctum plug according to claim 12, wherein:
said shaft portion of said plug is cylindrical.

15. A punctum plug according to claim 12, wherein:
said head portion of said plug is of a structure which sufficiently resists said head portion from being forced through a punctal sphincter muscle.

16. A punctum plug according to claim 12, wherein:
said body portion of said plug defines a conical section with an angle of between 50° and 60°.

17. A punctum plug according to claim 2, wherein:
said body portion of said plug defines a conical section with an angle of approximately 54°.

18. A punctum plug for insertion through a punctal opening at the eye, comprising:
   a) a shaft portion having first and second ends;
   b) a head portion coupled to said first end of said shaft portion; and
   c) a body portion coupled to said second end of said shaft portion, said body portion having a proximal side defining a substantially planar annular shelf,
      wherein said plug is sized to fit within the punctal opening and defines a bore having a proximal length with a first diameter and an adjacent relatively distal length which includes a plurality of portions in successively decreasing diameter relative to said first diameter, and
      wherein said body is solid radially outward from said bore.

19. A punctum plug according to claim 18, wherein:
said shaft portion of said plug is cylindrical.

20. A punctum plug according to claim 18, wherein:
said head portion of said plug is of a structure which sufficiently resists said head portion from being forced through a punctal sphincter muscle.

21. A punctum plug according to claim 18, wherein:
said body portion of said plug defines a conical section with an angle of between 50° and 60°.

22. A punctum plug for insertion through a punctal opening at the eye, comprising:
   a) a head;
   b) a body; and
   c) a shaft extending between said head and body portions, a shelf being defined adjacent a junction of the shaft and body portions, said shaft having a portion which tapers in a direction from said body to said head, said shaft further defining a circumferential groove at said junction with said body.

23. A punctum plug according to claim 22, wherein:
said plug defines an axial bore having a length and a non-uniform diameter along said length.

24. A method of inserting a punctum plug into a punctum of an eye, the punctum having an opening surrounded by a punctal ring, comprising:
   a) providing a punctum plug mounted on an insertion instrument having no moving parts, the punctum plug having a head portion, a substantially frustoconical body portion, and a shaft portion therebetween, a shelf being defined adjacent a junction of the shaft and body portions, and a bore being defined along a longitudinal axis of the plug, and the insertion instrument being frictionally engaged within the bore;
   b) inserting the plug without dilation into the punctal opening until the shelf of the plug is located below the punctal ring of the punctum; and
   c) without applying a stabilizing force to the head of the plug, withdrawing the insertion instrument without significant lateral movement to the instrument so as to release the instrument from engagement with the plug.

* * * * *